United States Patent [19]

Gaffney

[11] Patent Number: 4,499,323

[45] Date of Patent: Feb. 12, 1985

[54] METHANE CONVERSION

[75] Inventor: Anne M. Gaffney, West Chester, Pa.

[73] Assignee: Atlantic Richfield Company, Los Angeles, Calif.

[21] Appl. No.: 600,665

[22] Filed: Apr. 16, 1984

[51] Int. Cl.$^3$ .............................................. C07C 2/00
[52] U.S. Cl. ................................ 585/500; 585/415; 585/417; 585/541; 585/654; 585/656; 585/700; 585/943
[58] Field of Search ............... 585/500, 415, 417, 418, 585/654, 656, 658, 661, 541, 700, 943

[56] References Cited

U.S. PATENT DOCUMENTS

| | | | |
|---|---|---|---|
| 4,205,194 | 5/1980 | Mitchell et al. | 585/500 |
| 4,239,658 | 12/1980 | Mitchell et al. | 585/500 |
| 4,433,648 | 4/1984 | Jones et al. | 585/500 |
| 4,443,645 | 4/1984 | Jones et al. | 585/500 |

FOREIGN PATENT DOCUMENTS 747847 7/1980 U.S.S.R. .

OTHER PUBLICATIONS

Keller, G. E., "Synthesis of Ethylene via Oxidative Coupling of Methane," J. of Catalysis, 73, 9–19 (1982).
Chem. Abstracts 93:87561t (1980).

*Primary Examiner*—Delbert E. Gantz
*Assistant Examiner*—Cynthia A. Prezlock
*Attorney, Agent, or Firm*—Craig E. Larson

[57] ABSTRACT

A method for synthesizing hydrocarbons from a methane source which comprises contacting methane with an oxide of Pr having combined therewith an amount of alkali and/or alkaline earth metal which is sufficient to improve the selectivity to higher hydrocarbon products. The oxide is reduced by the contact which is carried at about 500° to 1000° C. Reducible oxides of Pr are regenerated by oxidizing the reduced composition with oxygen. The oxide $Pr_6O_{11}$ is particularly effective in the process.

31 Claims, No Drawings

METHANE CONVERSION

BACKGROUND OF THE INVENTION

1. Field of the Invention

This invention relates to synthesis of hydrocarbons from a methane source. A particular application of this invention is a method for converting natural gas to a more readily transportable material.

2. Description of the Prior Art

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion to olefins such as ethylene or propylene would be extremely valuable to the chemical industry.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony and bismuth are most useful. See commonly assigned U.S. Pat. Nos. 4,443,649; 4,444,984; 4,443,648; 4,443,645; 4,443,647; 4,443,644; and 4,443,646.

Commonly-assigned U.S. patent application Ser. No. 522,935, filed Aug. 12, 1983, discloses and claims a process which comprises contacting methane with an oxidative synthesizing agent under elevated pressure (e.g., 2–100 atmospheres) to produce greater amounts of $C_3+$ hydrocarbon products. The entire content of this application is incorporated herein by reference.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone. The entire content of this application is incorporated herein by reference.

Commonly-assigned U.S. patent application Ser. No. 522,937, filed August 12, 1983, discloses and claims a process for the conversion of methane to higher hydrocarbons which comprises contacting methane with an oxidative synthesizing agent containing a promoting amount of alkali metal and/or compounds thereof. The entire content of this application is incoporated herein by reference.

Commonly-assigned U.S. patent application Ser. No. 522,936, filed Aug. 12, 1983, discloses and claims a process for the conversion of methane to higher hydrocarbons which comprises contacting methane with an oxidative synthesizing agent containing a promoting amount of alkaline earth metal and/or compounds thereof. The entire content of this application is incorporated herein by reference.

SUMMARY OF THE INVENTION

It has now been found that methane may be converted to higher hydrocarbon products by contacting a methane-containing gas with a solid comprising: (1) a reducible oxide of praseodymium and (2) at least one member of the group consisting of alkali metals, alkaline earth metals, and compounds thereof. Alkali metals are selected from the group consisting of Li, Na, K, Rb and Cs. Alkaline earth metals are selected from the group consisting of Mg, Ca, Sr and Ba.

Methane is desirably contacted with the solid at a temperature within the range of about 500° to 1000° C. The atomic ratio of praseodymium to alkali metal or alkaline earth metal is desirably within the range of about 1–15:1. Hydrocarbons produced by the process may include lower alkanes, lower olefins and aromatics. The praseodymium oxide is reduced by contact with methane and is reoxidizable by contact with an oxygen-containing gas.

Contacting methane with oxides of Pr in the absence of an alkali metal or alkaline earth metal produces predominantly combustion products ($CO_x$) from methane. However, it has been found that incorporating an alkali metal or alkaline earth metal into the contact solid substantially reduces the formation of combustion products and improves higher hydrocarbon product selectivity.

DETAILED DESCRIPTION OF THE INVENTION

Reducible oxides of Pr can be supplied from a variety of known sources. The term "reducible" is used to identify those oxides which are reduced by contact with methane at temperatures within the range of about 500° to 1000° C. A preferred oxide is $Pr_6O_{11}$.

The contact solid employed in the present process contains, in addition to a reducible oxide of Pr, at least one alkali metal or alkaline earth metal. Alkali metals are preferred. Sodium and lithium are presently preferred alkali metals. The amount of alkali/alkaline earth metal incorporated into the contact solid is not narrowly critical. The preferred atomic ratio of the reducible praseodymium oxide component (expressed as the metal, Pr) to the alkali/alkaline earth metal component (expressed as the metal, e.g., Na) is within the range of about 1–15:1, more preferably within the range of about 1–3:1.

The contact solid may also contain other components heretofore referred to as oxidative synthesizing agents. Oxidative synthesizing agents generally comprise at least one oxide of at least one metal, which oxides when contacted with methane at synthesizing conditions (e.g., at a temperature selected within the range of about 500° to 1000° C.) produce higher hydrocarbon products, co-product water, and a reduced metal oxide. The composition thus contains at least one reducible oxide of at least one metal. The term "reducible" is used to identify those oxides of metals which are reduced by contacting methane at synthesizing conditions (e.g., at temperatures selected within the range of about 500°–1000° C.). The term "oxide(s) of metal(s)" includes: (1) one or more metal oxides (i.e., compounds described by the general formula $M_xO_y$ wherein M is a metal and the subscripts $x$ and $y$ designate the relative atomic proportions of metal and oxygen in the composition) and/or (2) one or more oxygen-containing metal compounds, provided that such oxides and compounds have the capability of performing to produce higher hydrocarbon products as set forth herein.

Oxidative synthesizing agents have previously been found to comprise reducible oxides of metals selected from the group consisting of Mn, Sn, In, Ge, Sb, Pb, and Bi and mixtures thereof. Particularly effective oxidative synthesizing agents have been found to comprise a reducible oxide of manganese and mixtures of a reducible oxide of manganese with other oxidative synthesizing agents.

It is within the scope of the present invention to include other effective oxidative synthesizing agent components with the combined praseodymium oxide/alkali-alkaline earth metal system of the present invention. Thus, the praseodymium oxide/alkali-alkaline earth metal system may also contain a reducible oxide selected from the group consisting of Mn, Sn, In, Ge, Sb, Pb, Bi and mixtures thereof.

It is also within the scope of the present invention to include at least one phosphorus component in the solid contacted with methane.

While the exact composition of the contact solids is more complex, the solids employed in the process of this invention may be described by the following empirical expression:

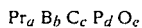
$Pr_a B_b C_c P_d O_e$ wherein B is selected from the group consisting of alkali and alkaline earth metals; C is selected from the group consisting of Mn, Sn, In, Ge, Pb, Sb, Bi and mixtures thereof; a, b, c, d and e indicate the atomic ratio of each component; and when a is 10, b is within the range of about 0.5–10, c is within the range of about 0–10, d is within the range of about 0–10, and e has a value which is determined by the valences and proportions of the other elements present.

These components may be associated with other support materials. However, in a presently preferred embodiment, a reducible oxide of Pr is employed as a support for the other components of the solids. While use of other supports is within the scope of this invention, it has been found that materials such as silica and alumina tend to deactivate the praseodymium component via the formation of silicates and aluminates.

A particularly preferred embodiment of the present invention comprises contacting methane at a temperature within the range of about 500° to 1000° C. with a solid comprising a member of the group consisting of alkali metals and compounds thereof associated with a support comprising a reducible oxide of Pr. Preferably, the reducible oxide of Pr comprises $Pr_6O_{11}$. Still more particularly, the presently preferred alkali metals associated with these supports are Na and Li.

The contact solids employed in this invention can be prepared by any suitable method. Conventional methods such as precipitation, co-precipitation, impregnation, or dry-mixing can be used. Supported solids may be prepared by methods such as adsorption, impregnation, precipitation, co-precipitation, and dry-mixing. When phosphorus is incorporated in the agent, it is desirable to provide it in the form of a phosphate of an alkali metal or an alkaline earth metal. Substantially any compound of these elements can be employed in the preparation of the promoted synthesizing agent.

A suitable method of preparation is to impregnate a support with solutions of compounds of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is prepared for use by calcining, preferably in air at a temperature selected within the range of about 300° to 1200° C. Particular calcination temperatures will vary depending upon the particular metal compound or compounds employed.

If phosphorus is used, the alkali/alkaline earth metal and phosphorus are preferably added to the composition as compounds containing both P and alkali/alkaline earth metals. Examples are the orthophosphates, metaphosphates, and pyrophosphates of alkali/alkaline earth metals. Pyrophosphates have been found to give desirable results. Sodium pyrophosphate is particularly preferred.

Regardless of how the components of the contact solid are combined, the resulting composite generally will be dried and calcined at elevated temperatures prior to use in the process of this invention.

The present process is distinguished from previously suggested methane conversion processes which rely primarily on interactions between methane and at least one of nickel and the noble metals, such as rhodium, palladium, silver, osmium, iridium, platinum and gold. An example of this type of process is disclosed in U.S. Pat. No. 4,205,194. The present process does not require that methane be contacted with one or more of nickel and such noble metals and compounds thereof.

Moreover, in a preferred embodiment, such contacting is carried out in the substantial absence of catalytically effective nickel and the noble metals and compounds thereof to minimize the deleterious catalytic effects of such metals and compounds thereof. For example, at the conditions, e.g., temperatures, useful for the contacting step of the present invention, these metals when contacted with methane tend to promote coke formation, and the metal oxides when contacted with methane tend to promote formation of combustion products ($CO_x$) rather than the desired hydrocarbons. The term "catalytically effective" is used herein to identify that quantity of one or more of nickel and the noble metals and compounds thereof which when present substantially changes the distribution of products obtained in the contacting step of this invention relative to such contacting in the absence of such metals and compounds thereof.

In addition to methane, the feedstock employed in the method of this invention may contain other hydrocarbon or non-hydrocarbon components, although the methane content should typically be within the range of about 40 to 100 volume percent, preferably from about 80 to 100 volume percent, more preferably from about 90 to 100 volume percent.

Operating temperatures for the contacting of methane-containing gas and the rare earth alkali metal solid are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 100 atmospheres, more preferably within the range of about 1 to 30 atmospheres.

Contacting methane and the solid comprising a praseodymium oxide/alkali-alkaline earth metal composite to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In carrying out the present process, a single reactor apparatus containing a fixed bed of solids may be used with intermittent or pulsed flow of a first gas comprising methane and a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising a reducible Pr oxide/alkali-alkaline earth metal composite to form higher hydrocarbon products, co-product water, and reduced metal oxide; (b) removing particles comprising reduced metal oxide from the first zone and contacting the reduced particles in a second zone with an oxygen-containing gas to form particles comprising a reducible Pr oxide/alkali-alkaline earth metal composite; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

Particles comprising a reducible Pr oxide/alkali alkaline earth metal composite which are contacted with methane may be maintained as fluidized, ebullating, or entrained beds of solids. Preferably methane is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In one more preferred embodiment of the present invention, methane feedstock and particles comprising a promoted oxidative synthesizing agent are continuously introduced into a methane contact zone maintained at synthesizing conditions. Synthesizing conditions include the temperatures and pressures described above. Gaseous reaction products from the methane contact zone (separated from entrained solids) are further processed—e.g., they are passed through a fractionating system wherein the desired hydrocarbon products are separated from unconverted methane and combustion products. Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative synthesizing agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

In one alternative process employing the method of this invention, a gas comprising oxygen may be co-fed with a hydrocarbon gas comprising methane to the methane contact zone. See U.S. patent application Ser. No. 600,656, the entire content of which is incorporated herein by reference.

In a further alternative process employing the method of this invention, the olefin content of the effluent produced by methane conversion as described herein may be oligomerized to produce normally liquid higher hydrocarbon products. See U.S. patent application Ser. No. 600,657, the entire content of which is incorporated herein by reference.

In a still further alternative process employing the method of this invention, it has been found advantageous to recover $C_2+$ alkanes from (1) the effluent produced by methane conversion as described herein and/or (2) streams derived from such effluent and to recycle such alkanes to the methane contact zone. See U.S. patent application Ser. No. 600,878, the entire content of which is incorporated herein by reference.

In a still further alternative process employing the method of this invention, it has been found that halogen promoters enhance results obtained when methane is converted to higher hydrocarbons by contact with a reducible metal oxide. See U.S. patent application Ser. No. 600,668, the entire content of which is incorporated herein by reference. Also see U.S. patent application Ser. Nos. 600,659 (chalcogen promoters) and 600,658 ($NO_x$ promoters), the entire contents of which are incorporated herein by reference.

The invention is further illustrated by reference to the following examples.

Methane-contact runs were made at about atmospheric pressure in quartz tube reactors (18 mm. inside diameter) packed with 10 ml. of contact solid. The reactors were brought up to temperature under a flow of nitrogen which was switched to methane at the start of the run. Unless otherwise indicated, all methane-contact runs described in the following examples had a duration of 2 minutes. At the end of each methane-contact run, the reactor was flushed with nitrogen and the solids were regenerated under a flow of air (usually at 800° C. for 30 minutes). The reactor was then again flushed with nitrogen and the cycle repeated. Most of the results reported below are based on the cumulative sample collected after the contact solid has been through at least one cycle of methane contact and regeneration.

Experimental results reported below include conversions and selectivities calculated on a carbon mole basis. Carbonate selectivities were calculated from the $CO_2$ content of the $N_2$ purge gas collected after the methane contact run.

Space velocities are reported as gas hourly space velocities (hr.$^{-1}$) and are identified as "GHSV" in the Examples.

EXAMPLE 1

A contact solid comprising sodium/Pr oxide was prepared by impregnating $Pr_6O_{11}$ with the appropriate amount of sodium (as sodium acetate) from water solutions. The impregnated solids were dried at 110° C. for 2 hours and then calcined in air by raising the temperature from 200° C. to 800° C. at a rate of about 100° C./hour and then holding the temperature at 800° C. for 16 hours. The calcined solids contained 4 wt. % Na. Results reported below in Table I are based on analyses of cumulative samples collected during a two-minute methane-contact run.

TABLE I

| | |
|---|---|
| Temp. (°C.) | 825 |
| GHSV (hr.$^{-1}$) | 2400 |
| % $CH_4$ Conv. | 36.4 |
| % $C_2+$ Sel. | 51.2 |
| % $CO_x$ Sel. | 45.0 |
| % Coke Sel. | 1.1 |

TABLE I-continued

| | |
|---|---|
| % Carbonate Sel. | 2.7 |

COMPARATIVE EXAMPLE A

The procedure described in Examples 1 was repeated except that calcined $Pr_6O_{11}$ was contacted with methane in the absence of sodium. Results are shown in Table II below.

TABLE II

| | |
|---|---|
| Temp. (°C.) | 825 |
| GHSV (hr.$^{-1}$) | 2400 |
| % $CH_4$ Conv. | 39.5 |
| % $C_2+$ Sel. | 1.0 |
| % $CO_x$ Sel. | 95.7 |
| % Coke Sel. | 1.5 |
| % Carbonate Sel. | 1.7 |

EXAMPLE 2

A number of methane contact runs over 4 wt. % $Na/Pr_6O_{11}$ (prepared as described in Examples 1) were performed to demonstrate the effect of temperatures and space velocities on process results. Results are shown in Table III below.

TABLE III

| Temp. (°C.) | 750 | 750 | 750 | 825 | 825 |
|---|---|---|---|---|---|
| GHSV(hr.$^{-1}$) | 1200 | 2400 | 4800 | 3600 | 4800 |
| % Conv. | 28.0 | 20.5 | 12.7 | 27.6 | 23.3 |
| % $C_2+$ Sel. | 67.3 | 76 | 84.1 | 62.6 | 69.4 |
| % $CO_x$ Sel. | 28.3 | 20.2 | 12.1 | 34.3 | 27.2 |
| % Coke Sel. | 1.2 | 0.8 | 1.0 | 0.9 | 1.2 |
| % Carbonate Sel. | 3.3 | 3.0 | 2.8 | 2.1 | 2.2 |

EXAMPLE 3

A contact solid comprising $NaMnO_2$/Pr oxide was prepared by impregnating $Pr_6O_{11}$ with the appropriate amount of sodium permanganate from a water solution. The calcined solids contained the equivalent of 10 wt. % $NaMnO_2$. Results reported below in Table IV are based on analyses of cumulative samples collected during two-minute methane runs at a temperature of 825° C. and 600 hr.$^{-1}$ GHSV.

TABLE IV

| | |
|---|---|
| % $CH_4$ Conv. | 80.9 |
| % $C_2+$ Sel. | 6.8 |
| % $CO_x$ Sel. | 89.9 |
| % Coke Sel. | 3.3 |

EXAMPLE 4

A lithium/praseodymium oxide solid was prepared by impregnating $Pr_6O_{11}$ with the appropriate amount of lithium (as lithium acetate) from water solutions. The dried, calcined solid contained 1.2 wt. % Li. When the solid was contacted with methane at 775° C. and 2400hr.$^{-1}$ GHSV, the following results were obtained: 21.7% methane conversion and 74.3% $C_2+$hydrocarbon selectivity. After 15 cycles of methane contact/air regeneration, the following results were obtained during the sixteenth methane contact run: 8.2% conversion and 89.4% $C_2+$hydrocarbon selectivity.

EXAMPLE 5

A potassium/praseodymium oxide solid was prepared by impregnating $Pr_6O_{11}$ with the appropriate amount of potassium (as potassium acetate) from water solutions. The dried, calcined solid contained 6.6 wt. % K. When the solid was contacted with methane at 775° C. and 2400 hr.$^{-1}$ GHSV, the following results were obtained: 28.6% methane conversion and 50.9% $C_2+$ hydrocarbon selectivity.

What is claimed is:

1. A method for converting methane to higher hydrocarbon products which comprises contacting at a temperature within the range of about 500°–1000° C. a gas comprising methane and a solid comprising:
   (a) a reducible oxide of Pr and
   (b) at least one member selected from the group consisting of alkali metals, alkaline earth metals, and compounds thereof;
provided that when said solid comprises an alkaline earth metal or compound thereof, said contacting is carried out in the substantial absence of catalytically effective Ni, Rh, Pd, Ag, Os, Ir, Pt, Au and compounds thereof.

2. The method of claim 1 wherein the solid is contacted with a gas comprising methane at a temperature within the range of about 700°–900° C.

3. The method of claim 1 wherein the gas comprising methane contains from about 40 to about 100 volume percent methane.

4. The method of claim 1 wherein the gas comprising methane contains from about 80 to about 100 volume percent methane.

5. The method of claim 1 wherein the gas comprising methane contains from about 90 to about 100 volume percent methane.

6. The method of claim 1 wherein the gas comprising methane is natural gas.

7. The method of claim 1 wherein the gas comprising methane is processed natural gas.

8. The method of claim 1 wherein component (b) of said solid is selected from the group consisting of alkali metals and compounds thereof.

9. The method of claim 8 wherein the alkali metal is selected from the group consisting of Li, Na, K, Rb, Cs, and compounds thereof.

10. The method of claim 8 wherein the alkali metal is selected from the group consisting of sodium, sodium compounds and mixtures thereof.

11. The method of claim 8 wherein the alkali metal is selected from the group consisting of potassium, potassium compounds and mixtures thereof.

12. The method of claim 8 wherein the alkali metal is selected from the group consisting of lithium, lithium compounds and mixtures thereof.

13. The method of claim 1 wherein the said reducible oxide and the alkali/alkaline earth metal are associated with a support material.

14. The method of claim 13 wherein said reducible oxide is provided as a support for at least one of the other components of said solid.

15. The method of claim 1 wherein the reducible oxide is $Pr_6O_{11}$.

16. The method of claim 1 wherein the atomic ratio of Pr to alkali/alkaline earth metal in said solid is within the range of about 1–15:1.

17. The method of claim 1 wherein the atomic ratio of Pr to alkali/alkaline earth metal in said solid is within the range of about 1–3:1.

18. The method of claim 1 wherein the said solid is described by the empirical formula:

$$Pr_a B_b C_c P_d O_e$$

wherein B is selected from the group consisting of alkali metals, alkaline earth metals, and mixtures thereof; C is selected from the group consisting of Mn, Sn, In, Ge, Pb, Sb, Bi and mixtures thereof; a, b, c, d, and e indicate the atomic ratio of each component; and when a is 10, b is within the range of about 0.5–10, c is within the range of about 0–10, d is within the range of about 0–10, and e has a value which is determined by the valences and proportions of the other elements present.

19. The method of claim 18 wherein the components are associated with a support material.

20. The method of claim 19 wherein a reducible oxide of Pr is provided as a support for the other components of said solid.

21. The method of claim 20 wherein C is Mn.

22. The method of claim 21 wherein B is Na.

23. The method of claim 21 wherein B is K.

24. The method of claim 21 wherein B is Li.

25. A method for synthesizing hydrocarbons from a methane source which comprises:
   (a) contacting at a temperature within the range of about 500°1000° C. a gas comprising methane and a solid comprising: (1) a reducible oxide of Pr and (2) at least one member of the group consisting of alkali metals, alkaline earth metals, and compounds thereof in an amount sufficient to improve the selectivity to higher hydrocarbons, said contacting producing $C_2+$ hydrocarbons, coproduct water and solids comprising a reduced Pr oxide, provided that when said solid comprises an alkaline earth metal or compound thereof, said contacting is carried out in the substantial absence of catalytically effective Ni, Rh, Pd, Ag, Os, Ir, Pt, Au and compounds thereof;
   (b) recovering $C_2+$ hydrocarbons;
   (c) at least periodically contacting the solids comprising reduced Pr oxide with an oxygen-containing gas to produce a solid comprising a reducible Pr oxide; and
   (d) contacting a gas comprising methane with the solids produced in step (c) as recited in step (a).

26. The method of claim 25 wherein the said solid of step (a) comprises an alkali metal or compound thereof.

27. The method of claim 25 wherein the said solid of step (a) comprises an alkali metal or compound thereof on a support consisting essentially of said reducible Pr oxide.

28. The method of claim 25 wherein the temperature of step (c) is within the range of about 300° to 1200° C.

29. A method for converting methane to higher hydrocarbon products which comprises contacting at a temperature within the range of about 500° to 1000° C. a gas comprising methane and a solid comprising a reducible oxide of Pr and at least one member of the group consisting of alkali metals and compounds thereof.

30. The method of claim 29 wherein the alkali metal component of said solid is selected from the group consisting of sodium, sodium compounds and mixtures thereof.

31. The method of claim 29 wherein the alkali metal component of said solid is selected from the group consisting of lithium, lithium compounds and mixtures thereof.

* * * * *